United States Patent
Nawaz et al.

(10) Patent No.: US 12,133,864 B1
(45) Date of Patent: *Nov. 5, 2024

(54) METHOD FOR TREATING CANCER CELLS WITH A CU/AG PARTICLE COMPOSITION

(71) Applicant: Imam Abdulrahman Bin Faisal University, Dammam (SA)

(72) Inventors: Muhammad Nawaz, Dammam (SA); Firdos Alam Khan, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/766,716

(22) Filed: Jul. 9, 2024

Related U.S. Application Data

(63) Continuation of application No. 18/599,582, filed on Mar. 8, 2024, now Pat. No. 12,090,169, which is a continuation of application No. 17/579,087, filed on Jan. 19, 2022, now Pat. No. 11,980,638.

(51) Int. Cl.
| | | |
|---|---|---|
| *A61K 33/38* | (2006.01) | |
| *A61K 9/14* | (2006.01) | |
| *A61P 35/00* | (2006.01) | |
| *C01B 25/45* | (2006.01) | |
| *C01G 3/02* | (2006.01) | |

(52) U.S. Cl.
CPC ............... *A61K 33/38* (2013.01); *A61K 9/14* (2013.01); *A61P 35/00* (2018.01); *C01B 25/45* (2013.01); *C01G 3/02* (2013.01); *C01P 2002/72* (2013.01); *C01P 2002/82* (2013.01); *C01P 2002/84* (2013.01); *C01P 2002/85* (2013.01); *C01P 2004/03* (2013.01); *C01P 2004/32* (2013.01); *C01P 2006/12* (2013.01); *C01P 2006/14* (2013.01); *C01P 2006/16* (2013.01)

(58) Field of Classification Search
None
See application file for complete search history.

(56) References Cited

U.S. PATENT DOCUMENTS

| | | | |
|---|---|---|---|
| 9,999,669 B1 * | 6/2018 | Ko | A61K 33/38 |
| 10,391,123 B2 * | 8/2019 | Liu | A61P 35/00 |
| 11,980,638 B2 * | 5/2024 | Nawaz | C01G 3/02 |
| 2012/0076832 A1 | 3/2012 | Petros | |
| 2012/0282327 A1 | 11/2012 | Hwu et al. | |
| 2019/0002317 A1 | 1/2019 | Salah | |

FOREIGN PATENT DOCUMENTS

| | | | |
|---|---|---|---|
| CN | 105195185 A | * | 12/2015 |
| CN | 107694582 A | | 2/2018 |

OTHER PUBLICATIONS

Mathew et al.; "Photoluminescence properties of Ag3PO4/CuO nanocomposites: Quantum Yield Effect," 2020; Elsevier; Optik, vol. 219, article 165282, pp. 1-8. (Year: 2020).*
Li et al.; "Application of silver phosphate-based photocatalysts: Barriers and solutions," 2019; Elsevier; Chemical Engineering Journal, vol. 366, pp. 339-357. (Year: 2019).*
Longo et al.; "Influence of Cu substitution on the structural ordering, photocatalytic activity and photoluminescence emission of Ag3-2xCuxPO4 powders," 2018; Elsevier; Applied Surface Science, vol. 440, pp. 61-72. (Year: 2018).*
Tamimi et al.; "Synthesis and analysis of silver-copper alloy nanoparticles of different ratios manifest anticancer activity in breast cancer cells," 2020; Cancer Nanotechnology, vol. 11, No. 13, pp. 1-16. (Year: 2020).*
Range et al.; "A continuous method to prepare poorly crystalline silver-doped calcium phosphate ceramics with antibacterial properties," 2015; RSC; RSC Advances, vol. 5, pp. 48172-43177. (Year: 2015).*
Mathew, et al. ; Photoluminescence properties of Ag3PO4/CuO nanocomposites: Quantum yield effect ; Optik vol. 2019 ; Oct. 2020; Abstract Only.
Al Tamimi, et al. ; Synthesis and analysis of silver-copper alloy nanoparticles of different ratios manifest anticancer activity in breast cancer cells ; Cancer Nanotechnology ; 2020 ; 16 Pages.
Martin et al.; "Efficient visible driven photocatalyst, silver phosphate: performance, understanding and perspective," 2015, RSC; Chem. Soc. Rev., vol. 44, pp. 7808-7828. (Year: 2015).
Zhang et al.; "In situ reduction of silver nanoparticles on hybrid polydopamine-copper phosphate nanoflowers with enhanced antimicrobial activity," 2017, RSC; Journal of Materials Chemistry B, vol. 5, pp. 5311-5317. (Year: 2017).
Ren et al.; "Characterisation of copper oxide nanoparticles for antimicrobial applications," 2009, Elsevier; International Journal of Antimicrobial Agents, vol. 33, pp. 587-590. (Year: 2009).

(Continued)

*Primary Examiner* — Tigabu Kassa
*Assistant Examiner* — Ivan A Greene
(74) *Attorney, Agent, or Firm* — Oblon, McClelland, Maier & Neustadt, L.L.P.

(57) ABSTRACT

A method of making Cu—$Ag_3PO_4$ nanoparticles is provided. The method includes forming a mixture of at least one silver salt, at least one phosphate salt, and at least one copper (II) salt. The method further includes dissolving the mixture in water. The method further includes sonicating the mixture. The method further includes precipitating the Cu—$Ag_3PO_4$ nanoparticles or "nanoparticles". The copper is present in the nanoparticles in an amount of 2 to 23 weight percent (wt. %) based on the total weight of the Cu—$Ag_3PO_4$. The nanoparticles of the present disclosure find application in treating cervical cancer, and colorectal cancer. The nanoparticles may also be used in photodegrading environmental pollutants.

7 Claims, 16 Drawing Sheets

(56) References Cited

OTHER PUBLICATIONS

Range et al.; "A continuous method to prepare poorly crystalline silver-doped calcium phosphate ceramics with antibacterial properties," 2015; RSC; RSC Advances, vol. 5, pp. 43172-43177. (Year: 2015).

Mathew et al.; "Photoluminescence properties of Ag3PO4/CuO nanocomposites: Quantum Yield Effect," 2020; Elsevier; Optik, vol. 219, article 165282, pp. 1-8. (Year: 2020).

Mak et al.; "Lost in traslation: animal models and clinical trials in cancer treatment," 2014; American journal of translational research , vol. 6, No. 2, pp. 114-118. (Year: 2014).

Cook et al.; "Predictive in vivo animal models and translation to clinical trials," 2012; Els ev i er; Drug Discovery Today, vol. 17, Nos. 5-6, pp. 253-260. (Year: 2012).

Raschke et al.; "Translating in vitro to in vivo and animal to human," 2020, Elsevier; Current Opinion in Toxcology, vols. 23-24, pp. 6-10. (Year: 2020).

Derwent English language Abstract for CN-105195185-A, pp. 1-2. (Year: 2015).

\* cited by examiner

METHOD FOR TREATING CANCER CELLS WITH A CU/AG PARTICLE COMPOSITION

CROSS-REFERENCE TO RELATED APPLICATIONS

The present application is a Continuation of U.S. application Ser. No. 18/599,582, now allowed, having a filing date of Mar. 8, 2024 which is a Continuation of U.S. application Ser. No. 17/579,087, now U.S. Pat. No. 11,980,638, having a filing date of Jan. 19, 2022.

BACKGROUND

Technical Field

The present disclosure is directed to a method for preparing nanoparticles, nanoparticles obtained by the method, pharmaceutical compositions containing the nanoparticles, and particularly to a method of preparing Cu—$Ag_3PO_4$ nanoparticles for treating cervical and colorectal cancers.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Treatments for cancers such as cervical cancer and colorectal cancer typically include surgery, radiation therapy, and/or chemotherapy. However, a continued high mortality of cancer patients reveals shortcomings of such treatments. Radiation therapy and chemotherapy have poor selectivity between cancerous and non-cancerous cells, thereby damaging healthy tissue. Many conventional anticancer pharmaceutical compositions for cancer treatments can suffer from the drawbacks of poor solubility, toxicity, and inefficacy. Therefore, treatments which can selectively target cancerous cells offer an advantage over the current technology.

Nanomaterials have the potential to selectively and directly target cancerous cells, leading to a decreased risk to healthy tissue in the patient and an overall increased chance of survival. Nanomaterials typically have unique properties over macromolecules, such as a high surface-to-volume ratio, enhanced electrical conductivity, superparamagnetic behavior, spectral shift of optical absorption, and unique fluorescence which allow them to be uniquely utilized in cancer treatment. Currently, nanomaterials are most commonly used in cancer treatments to enhance targeted drug delivery, and imaging.

Accordingly the present disclosure describes methods for making new nanomaterial compositions and the nanomaterial compositions obtained therefrom, where such nanomaterial compositions are easily synthesized, capable of selectively inducing toxicity to cancerous cells, and important to improving cancer treatment.

SUMMARY

The present invention provides a method of making Cu—$Ag_3PO_4$ nanoparticles and treating cancer using said nanoparticles. In an exemplary embodiment, a method of making Cu—$Ag_3PO_4$ nanoparticles is described. The method includes forming a mixture of at least one silver salt, at least one phosphate salt, and at least one copper (II) salt. The method further includes dissolving the mixture in water. The method further includes sonicating the mixture and precipitating the sonicated mixture to obtain the Cu—$Ag_3PO_4$ nanoparticles. Copper is present in the nanoparticles in an amount of 2 to 23 weight percent (wt. %) based on the total weight of the Cu—$Ag_3PO_4$.

In some embodiments, the method of forming the mixture includes dissolving the copper (II) salt in water to form a dissolved copper (II) salt. Subsequently, the silver salt is mixed into the dissolved copper (II) salt to form a solution. Furthermore, the phosphate salt is dissolved in water and mixed dropwise into the solution. The solution including the mixture of the three salts is then sonicated for at least one hour.

In some embodiments, the method further includes centrifuging the mixture and removing excess liquid from precipitated Cu—$Ag_3PO_4$ nanoparticles. The precipitated Cu—$Ag_3PO_4$ nanoparticles may be further washed with ethanol and water, followed by drying the washed Cu—$Ag_3PO_4$ nanoparticles at a temperature less than 150 degrees Celsius (° C.).

In some embodiments, the silver salt is silver nitrate, the phosphate salt is disodium hydrogen phosphate, and the copper (II) salt is copper (II) oxide (CuO). In some embodiments, the method of making the CuO includes dissolving copper nitrate trihydrate in water in a polytetrafluoroethylene (PTFE) or Teflon® lined autoclave to form a dissolved copper nitrate trihydrate. The method further includes mixing trisodium citrate and ammonium fluoride into the dissolved copper nitrate trihydrate at a temperature less than 23° C. to form a solution. The method further includes heating the solution in the PTFE or Teflon® lined autoclave at a temperature over 120° C. for more than 10 hours, followed by centrifuging the heated solution and removing excess liquid from a precipitate. The method further includes washing the precipitate with ethanol and water, followed by drying the washed precipitate at a temperature less than 150° C., and calcining the dried precipitate at a temperature greater than 300° C. to form CuO.

In some embodiments, the Cu—$Ag_3PO_4$ nanoparticles include a copper content of 2-7 wt. %, a mean surface area of 2.5-3.5-meter square per gram ($m^2/g$), a mean pore size of 20-30 nanometer (nm), and a mean pore volume of 100-200 centimeter cube per gram ($cm^3/g$).

In some embodiments, the Cu—$Ag_3PO_4$ nanoparticles include a copper content of 8-13 wt. %, a mean surface area of 3.8-4.8 $m^2/g$, a mean pore size of 25-35 nm, and a mean pore volume of 100-200 $cm^3/g$.

In some embodiments, the Cu—$Ag_3PO_4$ nanoparticles include a copper content of 14-18 wt. %. The Cu—$Ag_3PO_4$ nanoparticles further include a mean surface area of 5.5-6.5 $m^2/g$, a mean pore size of 15-25 nm, and a mean pore volume of 200-300 $cm^3/g$.

In some embodiments, the Cu—$Ag_3PO_4$ nanoparticles include a copper content of 19-23 wt. %. The Cu—$Ag_3PO_4$ nanoparticles further include a mean surface area of 6.5-7.5 $m^2/g$, a mean pore size of 20-30 nm, and a mean pore volume of 250-350 $cm^3/g$.

In some embodiments, the Cu—$Ag_3PO_4$ nanoparticles are substantially spherical and the Cu—$Ag_3PO_4$ nanoparticles have a mean particle size of 100-1000 nm.

In some embodiments, a method of treating cervical cancer, colorectal cancer, or both in a subject includes administering to the subject an effective amount of the Cu—$Ag_3PO_4$ nanoparticles prepared by the method of the present disclosure to decrease the average cancer cell viability by more than 10%.

In some embodiments, a cervical cancer treating composition includes 2-7 wt. % copper Cu—$Ag_3PO_4$ nanoparticles prepared by the method of the present disclosure. The composition has a half-maximal inhibitory concentration ($IC_{50}$) of 69-73 microgram per milliliter (μg/mL) for HeLa cells.

In some embodiments, a cervical cancer treating composition includes 8-13 wt. % copper Cu—$Ag_3PO_4$ nanoparticles prepared by the method of the present disclosure. The composition has a $IC_{50}$ of 95-105 μg/mL for HeLa cells.

In some embodiments, a cervical cancer treating composition includes 14-18 wt. % copper Cu—$Ag_3PO_4$ nanoparticles prepared by the method of the present disclosure. The composition has a $IC_{50}$ of 54-63 μg/mL for HeLa cells.

In some embodiments, a cervical cancer treating composition includes 19-23 wt. % copper Cu—$Ag_3PO_4$ nanoparticles prepared by the method of the present disclosure. The composition has a $IC_{50}$ of 45-55 μg/mL for HeLa cells.

In some embodiments, a colorectal cancer treating composition includes 2-7 wt. % copper Cu—$Ag_3PO_4$ nanoparticles prepared by the method of making Cu—$Ag_3PO_4$ nanoparticles. The composition has a $IC_{50}$ of 66-68 μg/mL for HCT-116 cells.

In some embodiments, a colorectal cancer treating composition includes 8-13 wt. % copper Cu—$Ag_3PO_4$ nanoparticles prepared by the method of the present disclosure. The composition has a $IC_{50}$ of 35-45 μg/mL for HCT-116 cells.

In some embodiments, a colorectal cancer treating composition includes 14-18 wt. % copper Cu—$Ag_3PO_4$ nanoparticles prepared by the method of the present disclosure. The composition has a $IC_{50}$ of 35-45 μg/mL for HCT-116 cells.

In some embodiments, a colorectal cancer treating composition includes 19-23 wt. % copper Cu—$Ag_3PO_4$ nanoparticles prepared by the method of the present disclosure. The composition has a $IC_{50}$ of 45-55 μg/mL for HCT-116 cells.

In another exemplary embodiment, a method of photodegrading environmental pollutants is described. The method of photodegrading environmental pollutants includes contacting the Cu—$Ag_3PO_4$ nanoparticles prepared by the method of the present disclosure and the environmental pollutant. The method of photodegrading environmental pollutants further includes exposing the solution to light and oxygen.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
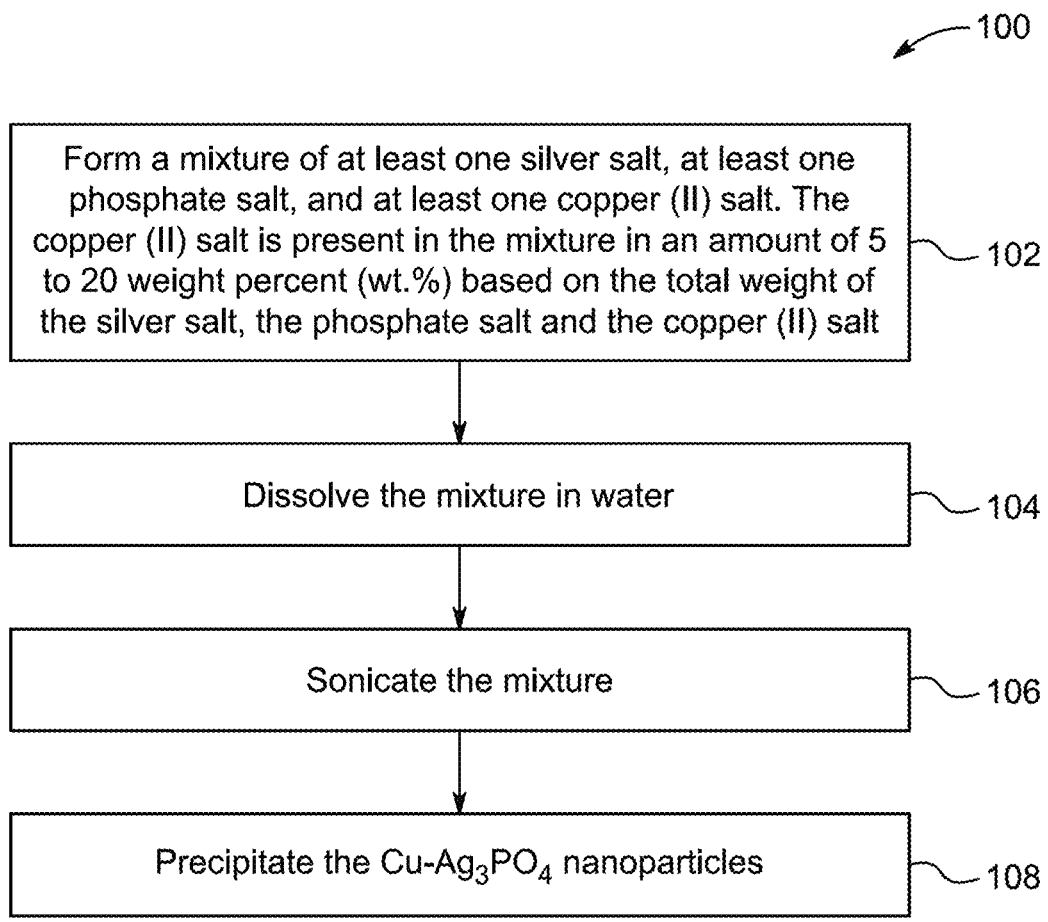
FIG. 1 is a schematic flow diagram of a method of making Cu—$Ag_3PO_4$ nanoparticles, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Embodiments of the present disclosure are directed to a method for making Cu—$Ag_3PO_4$ nanoparticles or "nanoparticles". The method is based on ultrasonic assisted synthesis of Cu—$Ag_3PO_4$ nanoparticle-containing compositions of varying copper concentrations, particularly, 5% Cu—$Ag_3PO_4$, 10% Cu—$Ag_3PO_4$, 15% Cu—$Ag_3PO_4$, and 20% Cu—$Ag_3PO_4$, respectively. The prepared nanoparticles were characterized by various analytical techniques, and their impact on cancer cells was studied. Although the description herein refers to the use of the nanoparticles for treatment of cervical and colon cancers, it may be understood by a person skilled in the art, that aspects of the present disclosure may be directed towards treatment of other cancers such as, cancer of thyroid, endocrine system, brain, breast, cervix, ovary, sarcoma, stomach, uterus medulloblastoma, colon, head and neck, liver, kidney, lung, non-small cell lung, melanoma, mesothelioma, or pancreatic cancer, as well. Cell viability studies with the nanoparticles of the present disclosure demonstrated that a significant decrease in cell viability was observed on both colon cancer (HCT-116) and cervical cancer (HeLa) cells, after the cells were treated with the nanoparticles prepared by the process of the present disclosure. The nanoparticles prepared by the process of the present disclosure are effective on both colon cancer, and cervical cancer cells at low concentrations (μg/mL), thereby circumventing the drawbacks such as drug induced toxicity, of the prior art.

Referring to FIG. 1, a schematic flow diagram of a method 100 of making Cu—$Ag_3PO_4$ nanoparticles is illustrated. The method 100 is described with reference to formation of CuO illustrated in FIG. 2. The order in which the method 100 is described is not intended to be construed as a limitation, and any number of the described method steps can be combined in any order to implement the method 100. Additionally, individual steps may be removed or skipped from the method 100 without departing from the spirit and scope of the present disclosure.

At step 102, the method 100 includes forming a mixture of at least one silver salt, at least one phosphate salt, and at least one copper (II) salt. The silver salt can be silver halide, silver sulfate, silver phosphate, silver carbonate, silver acetate, or a silver nitrate, and hydrates thereof.

In an embodiment, the silver salt is silver nitrate. The phosphate salt can be alkali metals or alkaline earth metals, with monophosphates, diphosphates, or polyphosphates, and hydrates thereof. In an embodiment, the phosphate salt is disodium hydrogen phosphate. The copper (II) salt can be oxides, hydroxides, carbonates, sulfates, halides, or nitrates of copper, and hydrates thereof. In an embodiment, the copper salt is copper (II) oxide (CuO).

At step 104, the method 100 includes dissolving the mixture in water. In an embodiment, each of the salts, namely, the copper salt, phosphate salt, and the silver salt, may be dissolved in water individually or in combination. In an embodiment, the copper (II) salt is dissolved in water to form a dissolved copper (II) salt. To the dissolved copper (II) salt, was added the silver salt to form a solution. In an embodiment the solution was then exposed to ultraviolet radiation, 200-400 nm at 36 W for 5 minutes. The phosphate salt, dissolved in water, was added to the solution in a dropwise manner.

At step 106, the method 100 includes sonicating the mixture. The solution containing the mixture of the three salts, namely, the copper salt, phosphate salt, and the silver salt, is sonicated for at least one hour. Sonication can take place at a frequency greater than 20 kilohertz (kHz), preferably 20-60 kHz, and a power of 90-250 watts (W). In an embodiment, the solution is sonicated for 1 hour at a frequency of 20 kHz, and a power of 125 W. Advantageous combinations of pore size and pore volume are obtained under particular sonication conditions including the amount of copper. Sonication in combination with exposure to ultraviolet light having a wavelength of in the range of 200-400 nm, desirably forms nanoparticles having a combination of large pore size and small pore volume. Sonication and UV light exposure may occur concurrently. UV light exposure is preferably carried out for a fraction of sonication time. For example, sonication of a mixture of metal salts for one hour preferably includes no more than 10% of total sonication time during which exposure to UV light occurs. Preferably, UV light exposure is conducted for a period of time that is 5-10% of the total time of sonication.

At step 108, the method 100 includes precipitating the Cu—Ag$_3$PO$_4$ nanoparticles. The nanoparticles were precipitated by addition of a non-solvent. The non-solvent can be a non-polar solvent such as but not limited to, alkanes such as pentane, hexane, and heptane, benzene, toluene, xylene, chloroform, diethyl ether, ethyl acetate, dichloromethane, and combinations thereof. The method 100 includes centrifuging the mixture at room temperature. The excess liquid was removed to obtain a precipitate of the Cu—Ag$_3$PO$_4$ nanoparticles. The precipitated nanoparticles may be further washed with a solvent. In an embodiment, the solvent is an alcohol or water or a combination of both. The alcohol can be ethanol, isopropyl alcohol, or any lower alcohol. In an embodiment, the solvent is ethanol and water. The washed nanoparticles may be further dried at a temperature less than 150° C. In an embodiment, the Cu—Ag$_3$PO$_4$ nanoparticles include a copper content of 2-7 wt. %. In an alternate embodiment, the Cu—Ag$_3$PO$_4$ nanoparticles include a copper content of 8-13 wt. %. In some embodiments, the Cu—Ag$_3$PO$_4$ nanoparticles include a copper content of 14-18 wt. %. In some embodiments, the Cu—Ag$_3$PO$_4$ nanoparticles include a copper content of 19-23 wt. %.

Figure 2:
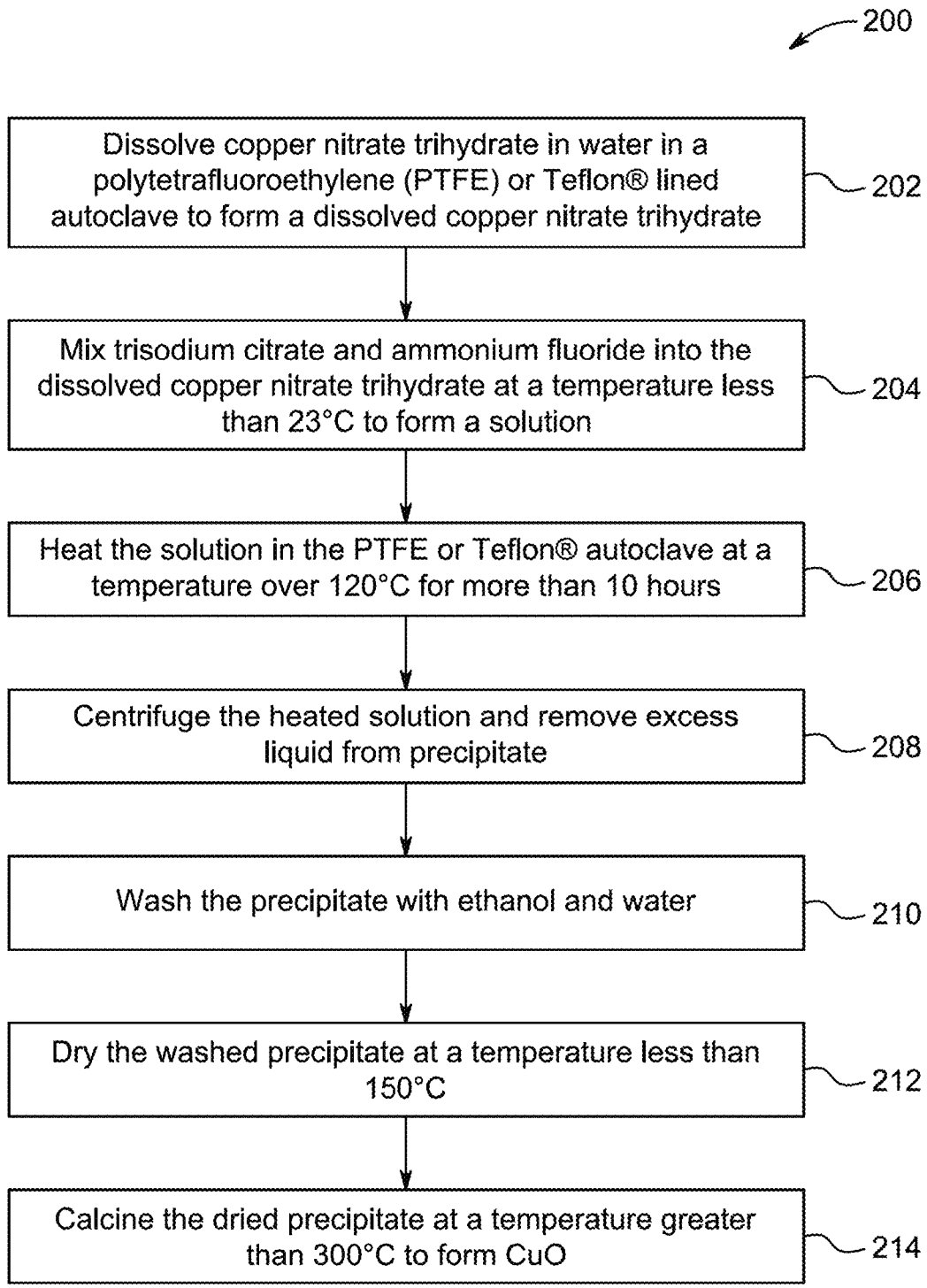
FIG. 2 is a schematic flow diagram of a method of making copper oxide (CuO), according to certain embodiments.

Referring to FIG. 2, a schematic flow diagram of a method 200 of making copper oxide (CuO) is illustrated. The order in which the method 200 is described is not intended to be construed as a limitation, and any number of the described method steps can be combined in any order to implement the method 200. Additionally, individual steps may be removed or skipped from the method 200 without departing from the spirit and scope of the present disclosure.

At step 202, method 200 includes dissolving copper nitrate trihydrate in water in an autoclave to form a dissolved copper nitrate trihydrate. In an embodiment, the autoclave is lined with polytetrafluoroethylene (PTFE) or Teflon®. In an embodiment, the dissolved copper nitrate trihydrate is obtained by heating copper nitrate trihydrate solution in the PTFE or Teflon® autoclave.

At step 204, method 200 includes mixing trisodium citrate and ammonium fluoride into the dissolved copper nitrate trihydrate at a temperature less than 23° C. to form a solution.

At step 206, method 200 includes heating the solution in the PTFE or Teflon® autoclave at a temperature over 120° C. for more than 10 hours.

At step 208, method 200 includes centrifuging the heated solution and removing excess liquid from precipitate.

At step 210, method 200 includes washing the precipitate with ethanol and water.

At step 212, method 200 includes drying the washed precipitate at a temperature less than 150° C.

At step 214, method 200 includes calcining the dried precipitate at a temperature greater than 300° C. to form CuO.

In some embodiments, the Cu—Ag$_3$PO$_4$ nanoparticles prepared by the method 100 have a mean surface area of 2.5-7.5 m$^2$/g, preferably 3.0-6.0 m$^2$/g, 3.5-5.5 m$^2$/g or 4.0-5.0 m$^2$/g. In some embodiments the nanoparticles have a mean pore size of 15-35 nm, preferably 17-27 nm, or 20-25 nm. In some embodiments the nanoparticles have a mean pore volume of 100-350 cm$^3$/g, preferably 150-300 cm$^3$/g, or 200-250 cm$^3$/g. In some embodiments, the Cu—Ag$_3$PO$_4$ nanoparticles are substantially spherical. In some embodiments, the Cu—Ag$_3$PO$_4$ nanoparticles have a mean particle size of 100-1000 nm, preferably 200-900 nm, 300-800 nm, 400-700 nm, or 500-600 nm. In one embodiment the nanoparticles have large pore size and small pore volume, for example, the pore size may range from 25-30 nm, preferably 26-29 nm or about 29.5 nm. Relatively large pore size contrasts with a pore volume that is relatively small, for example less than 0.015 cm$^3$/g, preferably from 0.01 to 0.15 cm$^3$/g. Relatively large pore size and small pore volume is indicative of a pore morphology that is wide and shallow. In this state the pore morphology may help docking with pharmaceutical materials and/or aid in approach to and ionic interaction/bonding with a cell or liposomal surface. This docking and/or bonding performance is especially noteworthy for HCT-116 cells.

In an aspect, the present disclosure provides a method of treating cervical cancer, colorectal cancer, or both in a subject by administering to the subject an effective amount of the Cu—Ag$_3$PO$_4$ nanoparticles prepared by the method 100. In the present embodiment, the subject is a human. In some embodiments, the subject may be an animal. Effective amount refers to a dose or concentration of a drug that produces a biological response. Herein the biological response refers to a decrease in cell viability following treatment with Cu—Ag$_3$PO$_4$ nanoparticles. The cell viability is the percentage of cells that survive following exposure to the nanoparticles. See Nawaz, et.al. Preparation of indium-cadmium sulfide nanoparticles with diverse morphologies: Photocatalytic and cytotoxicity study. Journal of Molecular Structure, 1253, (2022), 132288, incorporated herein by reference in its entirety. In an embodiment, the Cu—Ag$_3$PO$_4$ nanoparticles, prepared by the method 100, when administered to the subject decreases the average cancer cell viability by more than 10%, preferably 20% or more, 30% or more, 40% or more, 50% or more and most preferably leads to complete cell mortality.

The half-maximal inhibitory concentration (IC$_{50}$) was measured for the Cu—Ag$_3$PO$_4$ nanoparticles with HeLa cells, HCT-116 cells, HEK-293 cells. IC$_{50}$ is defined as the concentration of the Cu—Ag$_3$PO$_4$ nanoparticles administered to cells that will inhibit their growth by 50%. In some embodiments, the Cu—Ag$_3$PO$_4$ nanoparticles, prepared by the method 100, have an IC$_{50}$ of 30-110 µg/mL, preferably 40-100 µg/mL, 50-90 µg/mL, or 60-80 µg/mL. Lower IC$_{50}$ values indicate an affinity of the Cu—Ag$_3$PO$_4$ nanoparticles for the cells as a lower concentration is needed to decrease cell viability.

Further, the present disclosure provides a method of photodegrading environmental pollutants. The method includes contacting the Cu—Ag$_3$PO$_4$ nanoparticles prepared by the method 100 and the environmental pollutant in a solution. The method further includes exposing the solution to light and oxygen. In some embodiments, the environmental pollutant is in an aqueous solution. In some embodiments the Cu—Ag$_3$PO$_4$ nanoparticles are dispersed in water before contacting with the solution. In some embodiments the Cu—Ag$_3$PO$_4$ nanoparticles are stirred into the solution to increase contact probability with the environmental pollutant. In some embodiments the environmental pollutant is present in the solution at 400 ppm or more. In some embodiments 1-500 mg/L, preferably 100-400 mg/L, or 200-300 mg/L of Cu—Ag$_3$PO$_4$ nanoparticles are contacted with the solution. The environmental pollutant can be aldehydes such as acetaldehyde and formaldehyde, carboxylic acids such as acetic acid and formic acid, aromatic compounds such as benzene, toluene, xylene, and halogenated benzene, alkyl halides, alcohols, ketones, esters, and hydrocarbons. The light can be a wavelength between 200-800 nm, preferably 200-450 nm, more preferably 200-300 nm, based on the absorbance of the Cu—Ag$_3$PO$_4$ nanoparticles in FIG. 8.

EXAMPLES

The following examples describe and demonstrate exemplary embodiments of the Cu—Ag$_3$PO$_4$ nanoparticles described herein. The examples are provided solely for the purpose of illustration and are not to be construed as limitations of the present disclosure, as many variations thereof are possible without departing from the spirit and scope of the present disclosure.

Example 1: Materials Required

Precursor chemical salts such as copper nitrate trihydrate (CuH$_6$N$_2$O$_9$), trisodium citrate (Na$_3$C$_6$H$_5$O$_7$), ammonium fluoride (NH$_4$F), silver nitrate (AgNO$_3$) and disodium hydrogen phosphate (Na$_2$HPO$_4$) were used for Cu—Ag$_3$PO$_4$ nanoparticles synthesis. Further, water (H$_2$O) was also used.

Example 2: Method of Preparation of CuO 1 g copper nitrate trihydrate was dissolved in 30 mL of water in an autoclave lined with polytetrafluoroethylene (PTFE) or Teflon®, followed by addition of 0.3 g trisodium citrate and 0.3 g ammonium fluoride. The mixture was stirred at room temperature. Further, the autoclave was kept in an oven and heated at 150° C. for 15 hours. The autoclave was cooled at room temperature and precipitate was centrifuged, washed, dried, and calcined at 400° C. to give CuO (copper (II) oxide).

Example 3: Method of Preparation of Cu—Ag$_3$PO$_4$ Nanoparticles

To prepare Cu—Ag$_3$PO$_4$ nanoparticles, calculated amount of CuO (for 5, 10, 15 and 20%) based on the weight of Cu—Ag$_3$PO$_4$, was dissolved in 30 mL of water, to which was added 0.5 g silver nitrate, to form a solution. After stirring the solution to allow for complete dissolution, 0.3 g disodium hydrogen phosphate (Na$_2$HPO$_4$) dissolved in 10 mL of water was added in a dropwise manner to the solution. The solution was further stirred for further 5 minutes to obtain a mixture. The mixture was sonicated for 1 hour and centrifuged to separate the supernatant and the precipitate. The precipitate was washed and dried to obtain the nanoparticles. Hence, products obtained were named as 5% Cu—Ag$_3$PO$_4$, 10% Cu—Ag$_3$PO$_4$, 15% Cu—Ag$_3$PO$_4$, and 20% Cu—Ag$_3$PO$_4$.

EXPERIMENTAL

Experiment 1: In vitro cell culture and 3-(4,5-dimethyl-thiazol-2-yl)-2,5-diphenyl tetrazolium bromide (MTT) assay Samples were treated with cancer cell lines such as human colorectal cancer cells (HCT-116) and human cervical cancer cells (HeLa) to study viability and proliferation of such cells. 5% Cu—Ag$_3$PO$_4$, 10% Cu—Ag$_3$PO$_4$, 15% Cu—Ag$_3$PO$_4$, and 20% Cu—Ag$_3$PO$_4$, as obtained in Example 2, are collectively referred to as 'samples' and individually referred to as 'sample' unless otherwise specified. Non-cancer cell line such as embryonic kidney cells (HEK-293) was considered as a control cell line. The cells were cultured and maintained in Dulbecco's Modified Eagle Media (DMEM), L-glutamine (5%), penicillin (1%), streptomycin (1%), Fetal bovine serum (FBS) (10%), and selenium chloride (1%). The cells were grown in 96 well plates in a 5% CO$_2$ incubator (Thermo Fisher Scientific, Inc., Waltham, MA, USA) at 37° C., and 75-80% confluence cells and cell were processed for the MTT assay. The MTT assay is a colorimetric assay for measuring cell metabolic activity. The MTT assay is based on the ability of nicotinamide adenine dinucleotide phosphate (NADPH)-dependent cellular oxidoreductase enzymes to reduce the tetrazolium dye MTT to insoluble formazan, which has a purple colour.

The cells were treated with 5% Cu—Ag$_3$PO$_4$, 10% Cu—Ag$_3$PO$_4$, 15% Cu—Ag$_3$PO$_4$, and 20% Cu—Ag$_3$PO$_4$ with dosages ranging from 5.0 µg to 95 µg/mL for 48 hours. The treated cells were further processed to examine the cell viability using the MTT assay. The nanoparticles were not added to the control cell line. The embryonic kidney cells (HEK-293) were also treated with 5% Cu—Ag$_3$PO$_4$, 10% Cu—Ag$_3$PO$_4$, 15% Cu—Ag$_3$PO$_4$, and 20% Cu—Ag$_3$PO$_4$ with dosages ranging from 5.0 µg to 95 µg/mL. Both the control and treated groups (5% Cu—Ag$_3$PO$_4$, 10% Cu—Ag$_3$PO$_4$, 15% Cu—Ag$_3$PO$_4$, and 20% Cu—Ag$_3$PO$_4$) were treated with 10 µl of MTT (5 mg/mL), and cells were incubated in a CO$_2$ incubator for 4 hours. Further, cell culture media was replaced with DMSO (1%), and the 96-well plate was examined under an enzyme-linked immunoassay (ELISA) plate reader (Bio-tek Instruments, USA) at a wavelength of 570 nm. The percentage of cell viability was calculated for statistical analysis.

Experiment 2: Apoptotic DAPI (4',6-Diamidino-2-Phenylindole) Staining

Morphology of cancer nuclear structure changes due to treatments with 5% Cu—$Ag_3PO_4$, 10% Cu—$Ag_3PO_4$, 15% Cu—$Ag_3PO_4$, and 20% Cu—$Ag_3PO_4$. The morphology changes were examined by DAPI staining assay. HCT-116 cells were divided into two groups such as a control group and an experimental group. No nanoparticles were added to the control group. However, 5% Cu—$Ag_3PO_4$, 10% Cu—$Ag_3PO_4$, 15% Cu—$Ag_3PO_4$, and 20% Cu—$Ag_3PO_4$ (25 μg/mL) were added to the experimental group. Post 48 hours treatment, the control group and the experimental group were exposed to ice-cold (4%) paraformaldehyde and further with Triton X-100 in phosphate-buffered saline (PBS).

Further, the HCT-116 cells were stained with DAPI (1.0 μg/mL) for 5 minutes under a dark environment, and finally washed with PBS and cover-slipped. The deoxyribonucleic acid (DNA) staining was examined by using confocal scanning microscope (Zeiss, Germany). The data presented as mean (±) standard deviation (SD) obtained from triplicates and one-way analysis of variance (ANOVA) followed by Dennett's post hoc test with GraphPad Prism Software (GraphPad Software, USA) for final statistical analysis.

Figure 3:
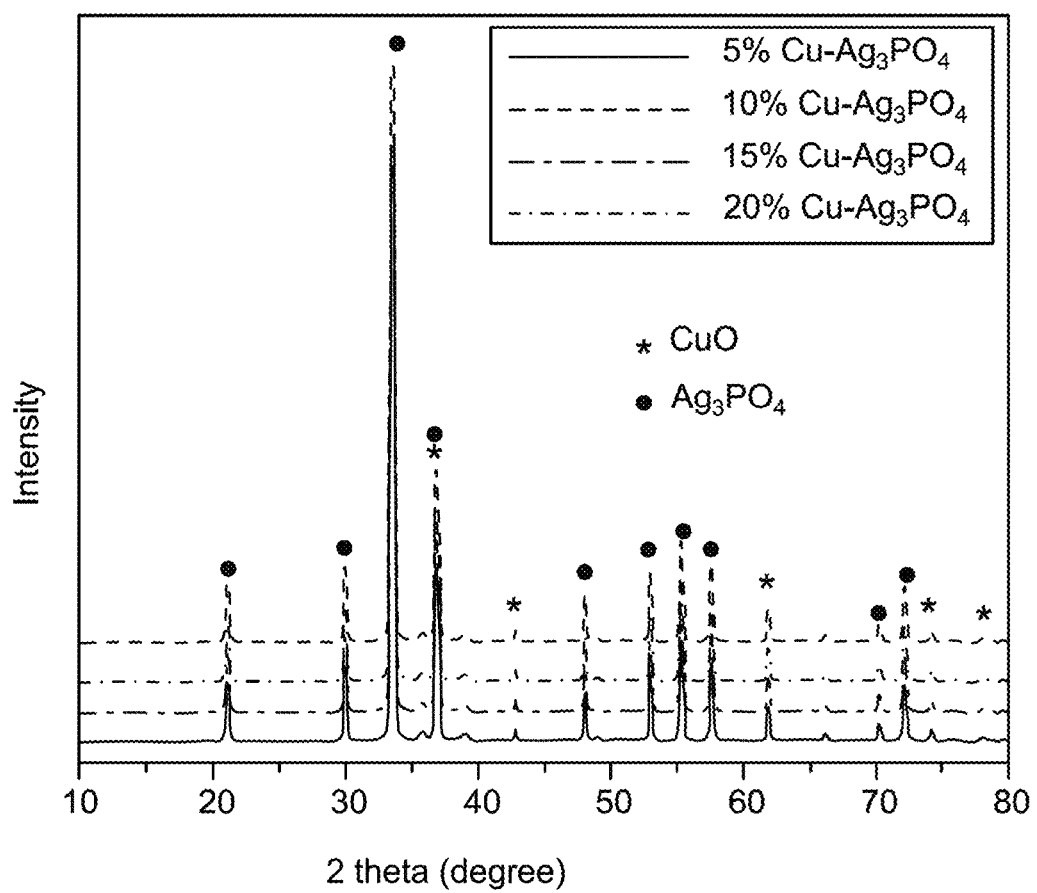
FIG. 3 is a combined X-Ray Diffraction (XRD) image of the Cu—$Ag_3PO_4$ nanoparticles with varying weight percentages, 5% Cu—$Ag_3PO_4$ (3A), 10% Cu—$Ag_3PO_4$ (3B), 15% Cu—$Ag_3PO_4$ (3C) 20% Cu—$Ag_3PO_4$ nanoparticles (3D), according to certain embodiments.
Figure 4A:
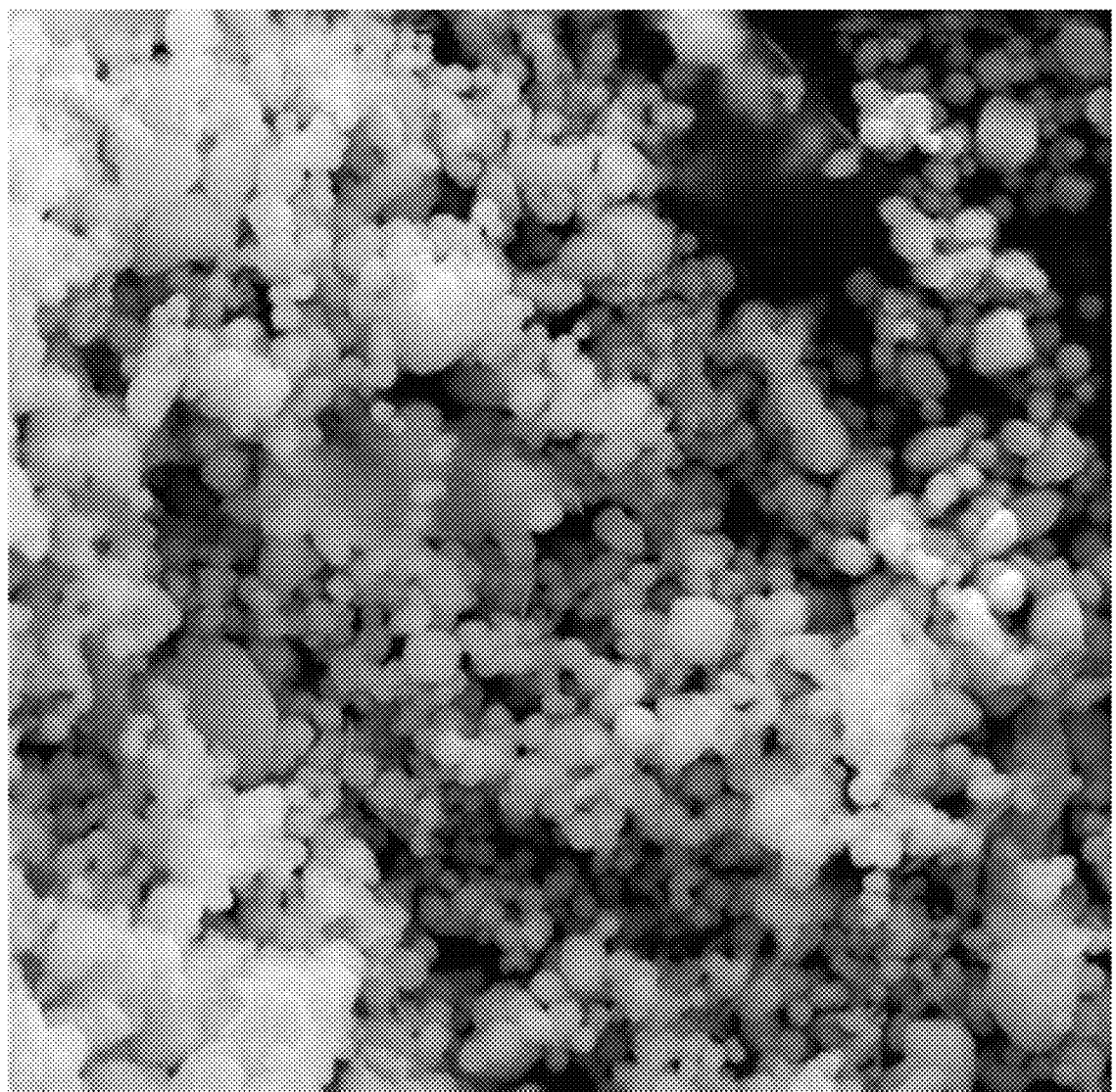
FIGS. 4A-4D are Scanning Electron Microscope (SEM) images of the Cu—$Ag_3PO_4$ nanoparticles with varying weight percentages, 5% Cu—$Ag_3PO_4$ (4A), 10% Cu—$Ag_3PO_4$ (4B), 15% Cu—$Ag_3PO_4$ (4C), 20% Cu—$Ag_3PO_4$ nanoparticles (4D), according to certain embodiments.
Figure 4B:
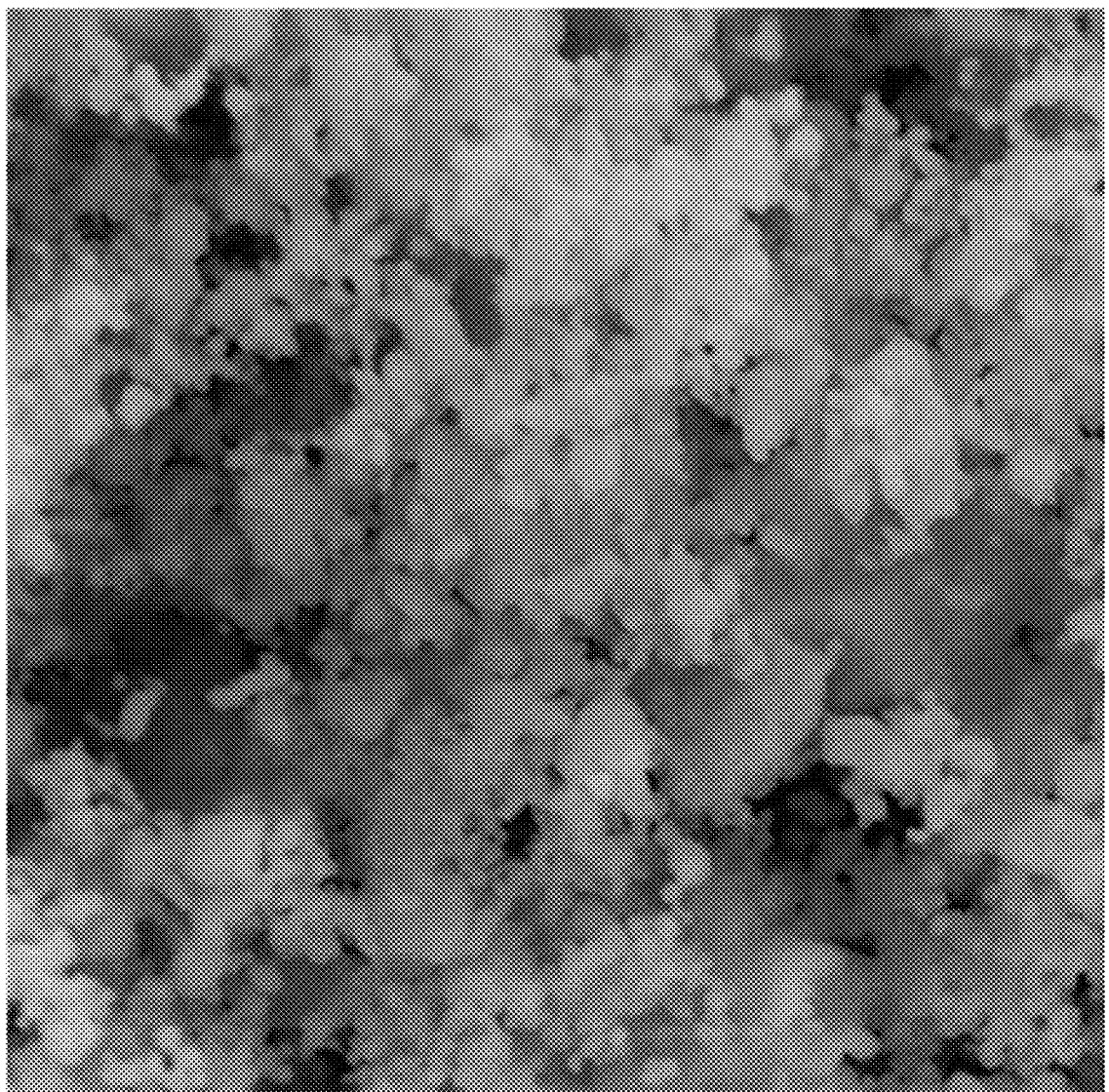
Figure 4C:
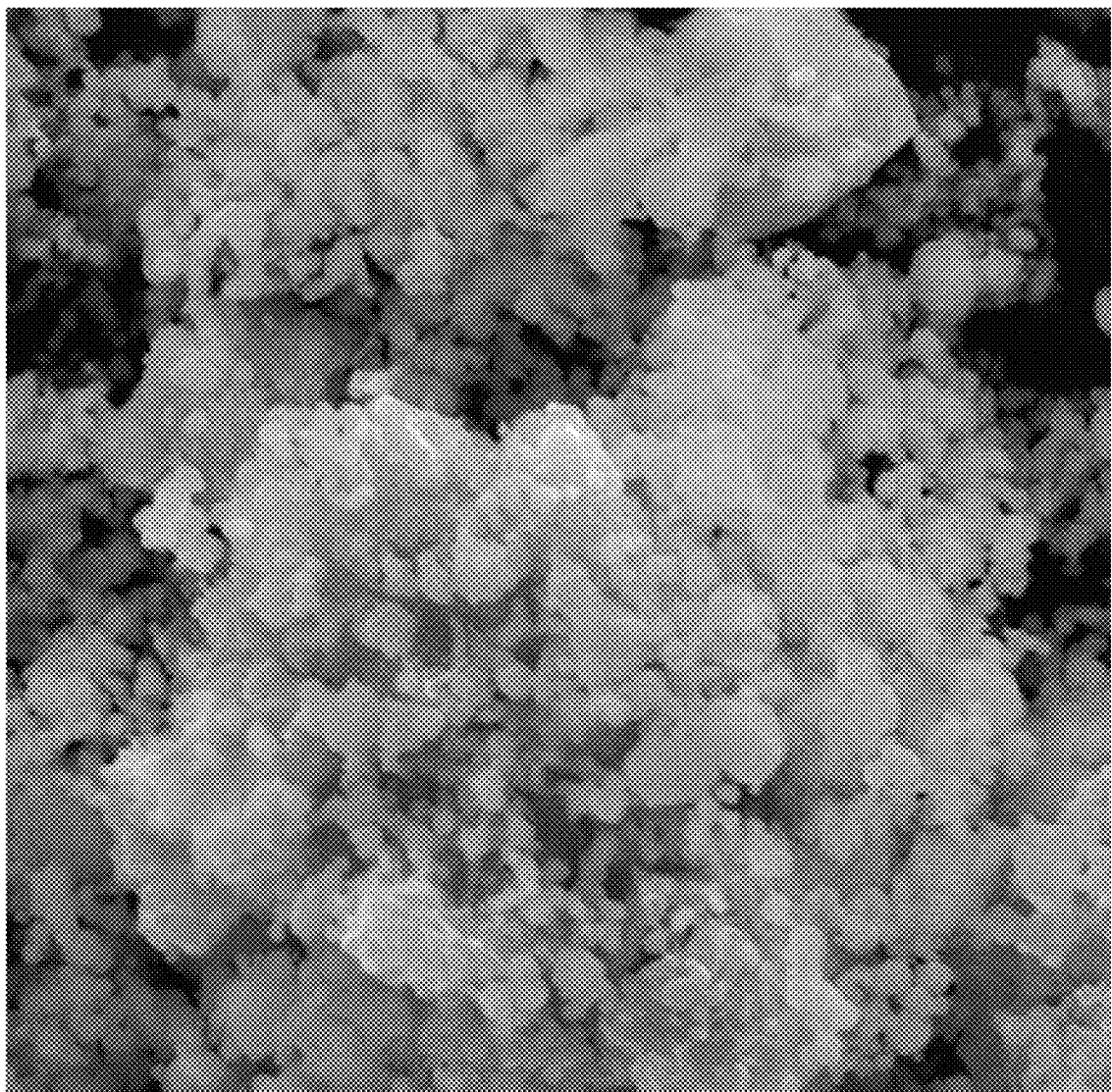
Figure 4D:
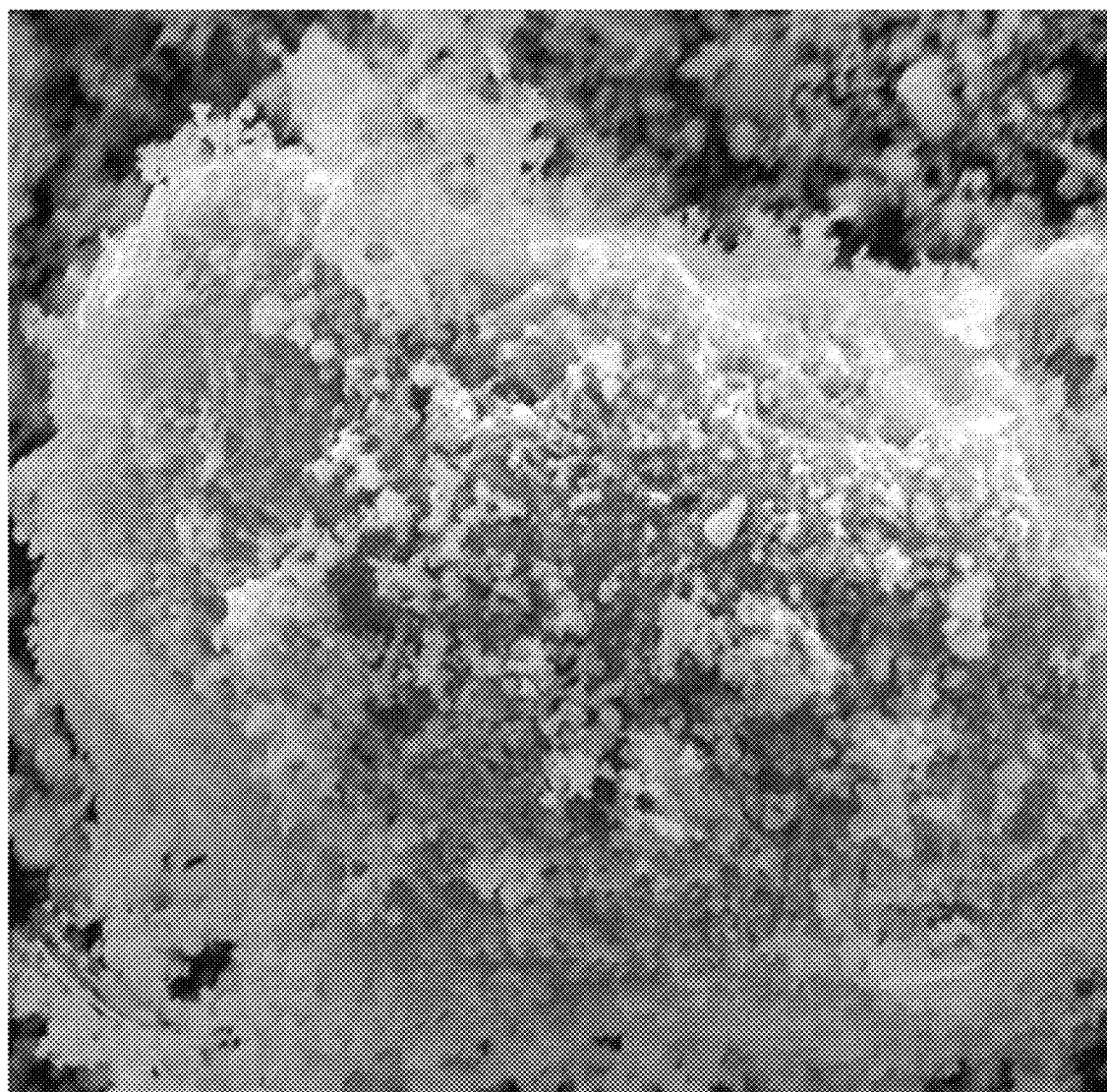
Figure 5A:
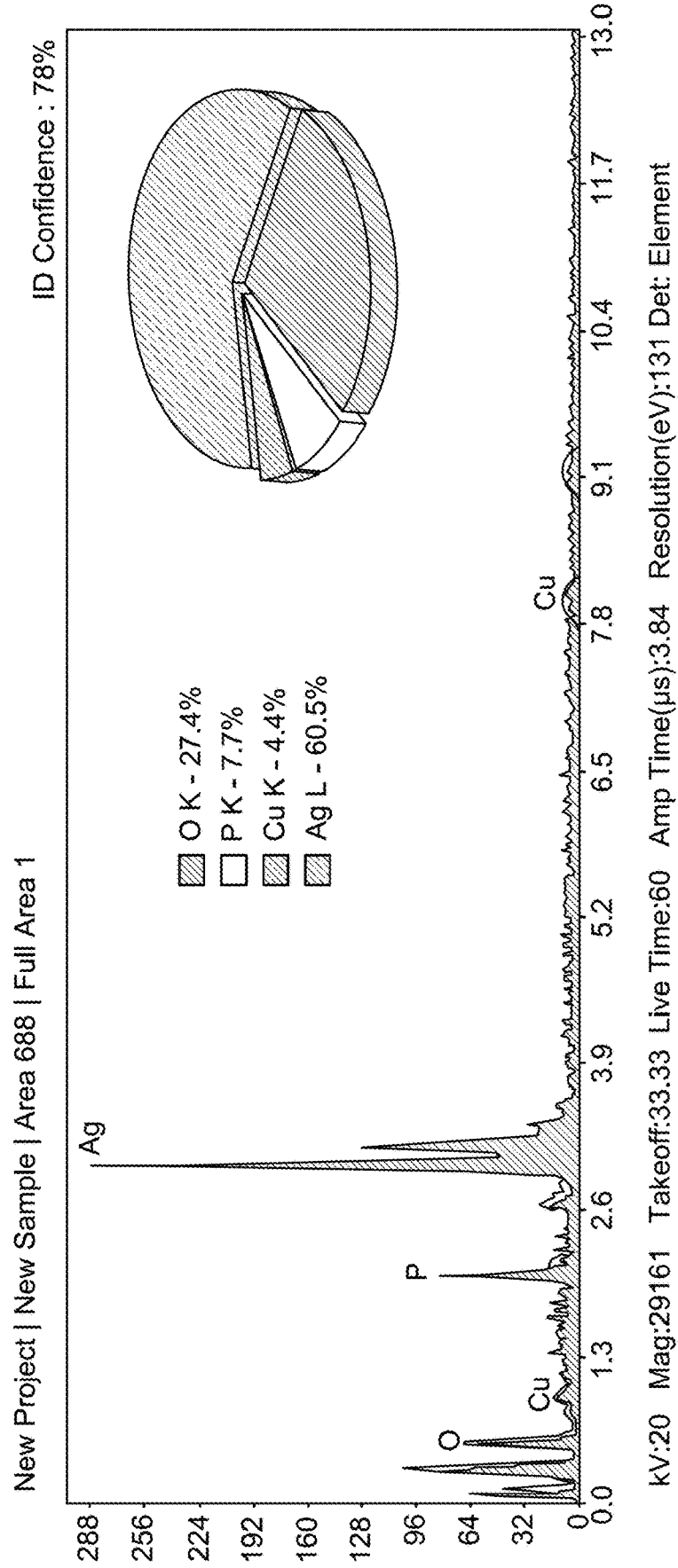
FIGS. 5A-5D are Energy Dispersive X-Ray Analysis (EDX) spectra and elemental mapping of the Cu—$Ag_3PO_4$ nanoparticles with varying weight percentages, 5% Cu—$Ag_3PO_4$ (5A), 10% Cu—$Ag_3PO_4$ (5B), 15% Cu—$Ag_3PO_4$ (5C), 20% Cu—$Ag_3PO_4$ nanoparticles (5D), according to certain embodiments.
Figure 5B:
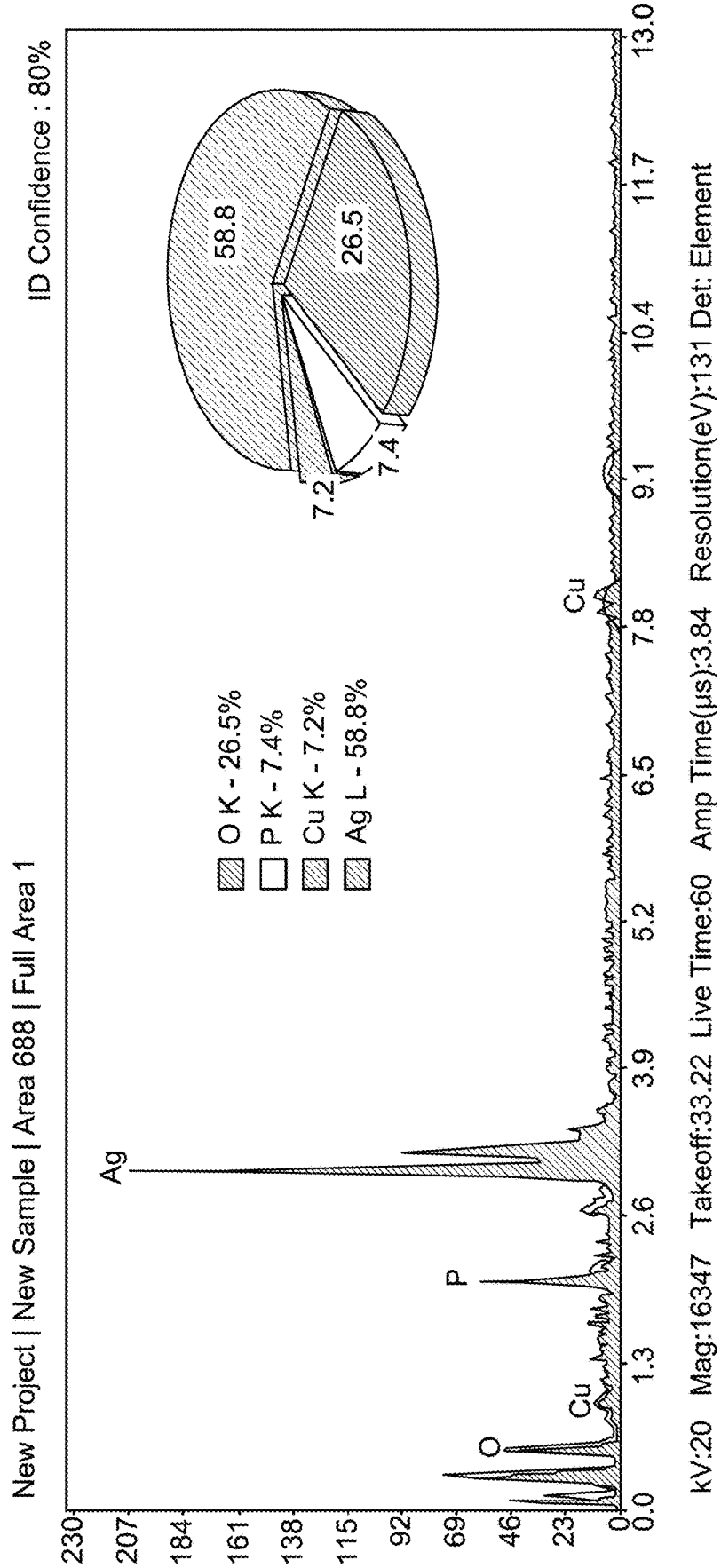
Figure 5C:
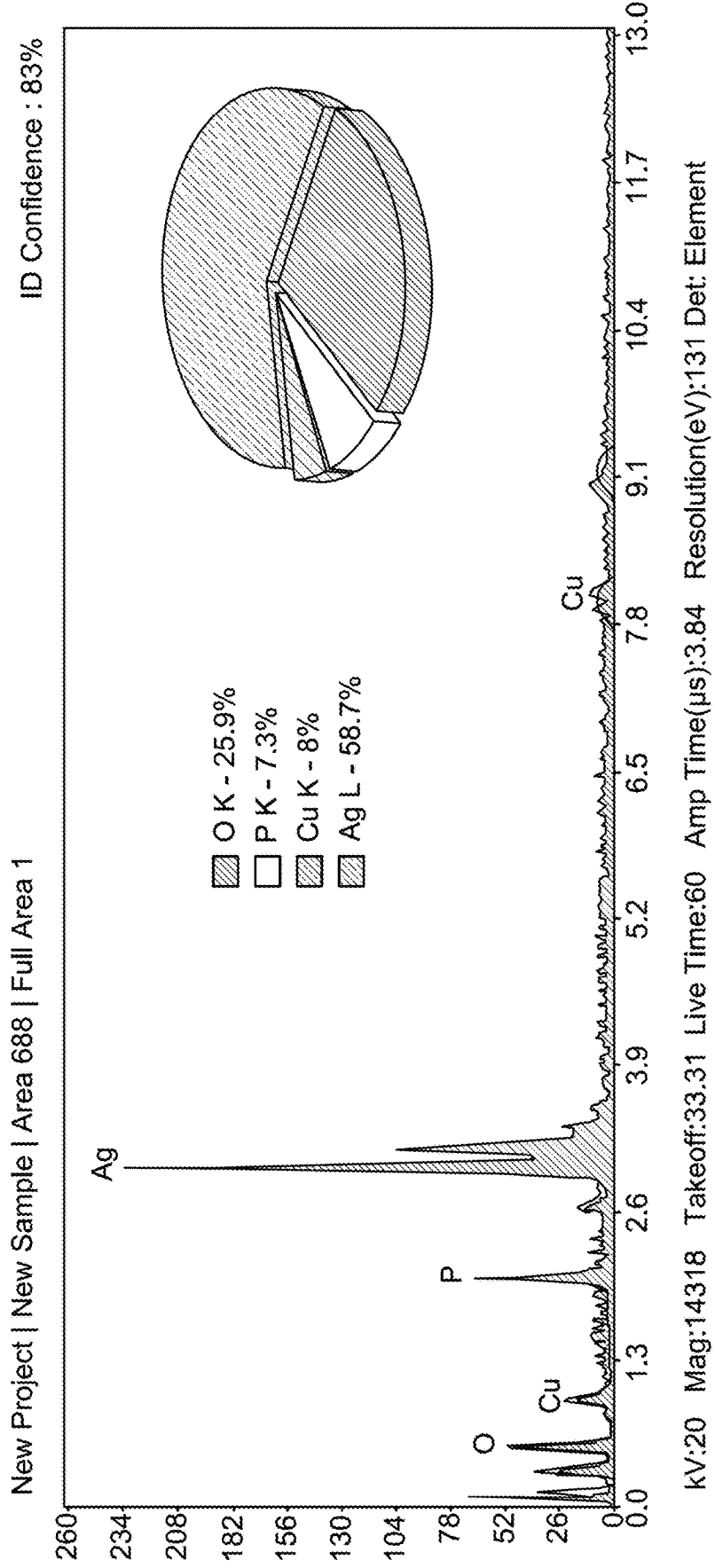
Figure 5D:
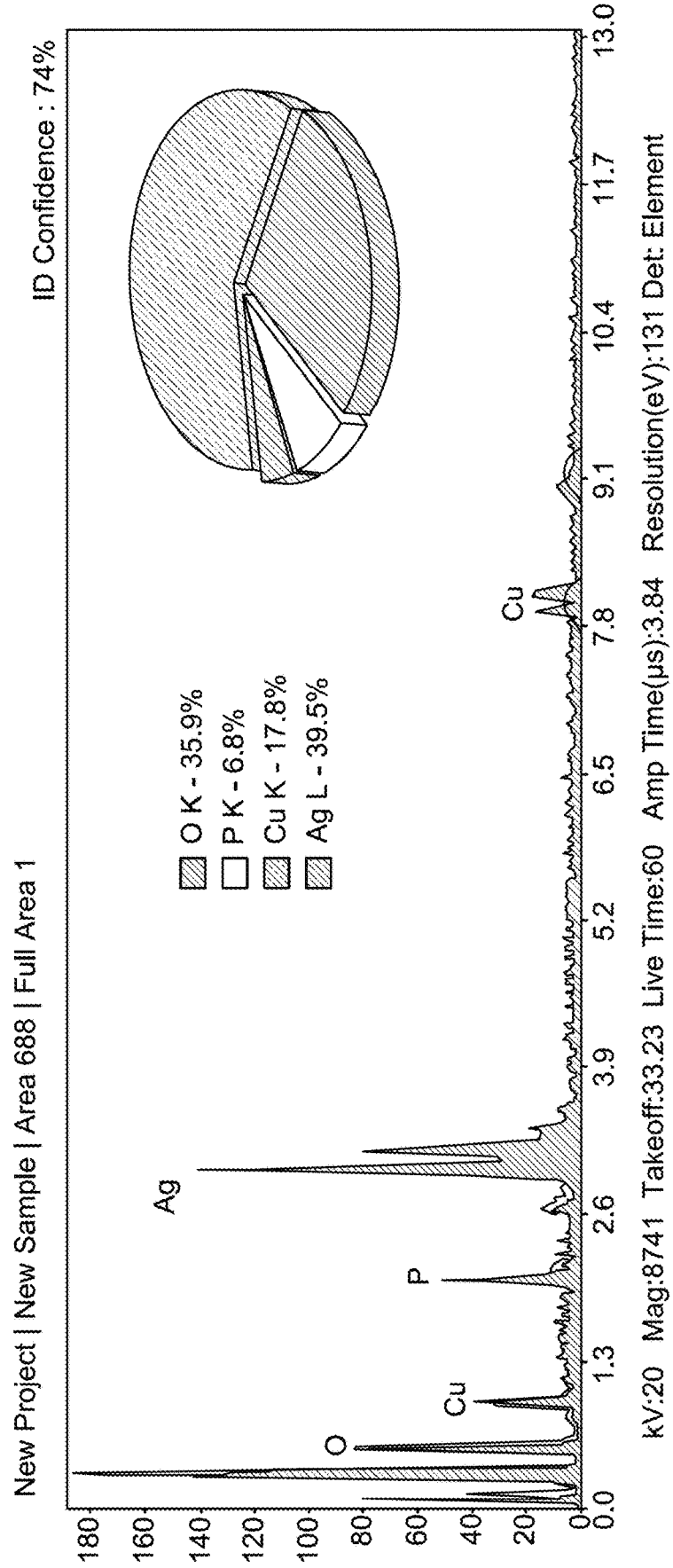

Referring to FIG. 3, an X-Ray Diffraction (XRD) image of 5% Cu—$Ag_3PO_4$, 10% Cu—$Ag_3PO_4$, 15% Cu—$Ag_3PO_4$, and 20% Cu—$Ag_3PO_4$ nanoparticles, is illustrated. The XRD is a technique employed to determine the underlying crystal structure of a material and enables verification of the crystallinity and structure of a sample. X-ray diffractometer (XRD, Rigaku, Japan) is used to study phases of Cu—$Ag_3PO_4$ nanoparticles in the range of 10-80° with 0.9°/minute scanning speed. From the FIG. 3, it can be observed that the material includes CuO, and $Ag_3PO_4$ particles which constitute to form Cu—$Ag_3PO_4$ nanoparticles.

Surface morphology and structure of the as-synthesized Cu—$Ag_3PO_4$ nanoparticles were evaluated by scanning electron microscopy (SEM) (Tscan); the images of which (5% Cu—$Ag_3PO_4$, 10% Cu—$Ag_3PO_4$, 15% Cu—$Ag_3PO_4$, and 20% Cu—$Ag_3PO_4$ nanoparticles) are presented in FIGS. 4A-4D, respectively. The nanoparticles are substantially spherical, however as the copper content increases the nanoparticles tend to aggregate to form clusters of particles. The average size of the nanoparticles is 400 nm, however there is a wide dispersion of sizes for the different copper contents.

Further, the elemental mapping of 5% Cu—$Ag_3PO_4$, 10% Cu—$Ag_3PO_4$, 15% Cu—$Ag_3PO_4$, and 20% Cu—$Ag_3PO_4$ nanoparticles was performed by Energy Dispersive X-ray spectroscopy (EDS) is to identify and quantify elemental compositions in the nanoparticles; the results of the present study are presented in FIG. 5A to 5D. The presence of 4 peaks between 0.5 KeV and 4 KeV can be attributed to copper, silver, phosphorous and oxygen, confirming the formation of the nanoparticles. Quantitative analysis of the EDS spectra proved a high presence silver, and other elements being copper, phosphorous and oxygen, confirming the formation Cu—$Ag_3PO_4$ nanoparticles.

Figure 6:
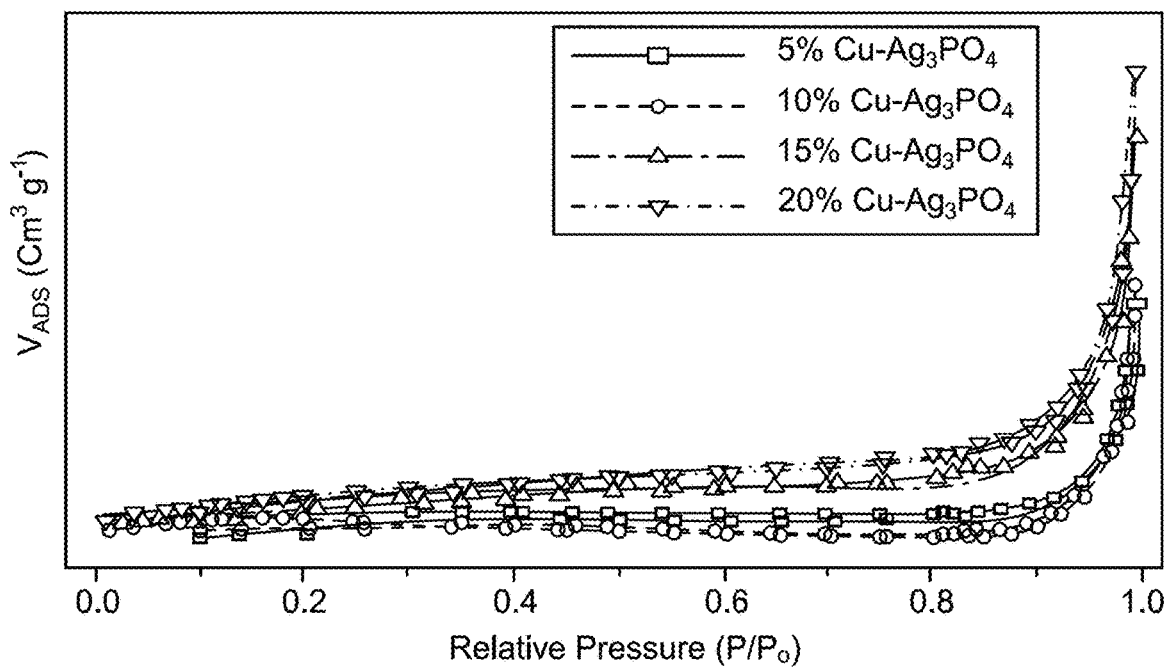
FIG. 6 is a graphical representation of $N_2$ adsorption-desorption isotherms for the Cu—$Ag_3PO_4$ nanoparticles with varying weight percentages, according to certain embodiments.

Referring to FIG. 6, a graphical representation of $N_2$ adsorption-desorption isotherms for 5% Cu—$Ag_3PO_4$, 10% Cu—$Ag_3PO_4$, 15% Cu—$Ag_3PO_4$, and 20% Cu—$Ag_3PO_4$ (samples) nanoparticles is illustrated. A $N_2$ adsorption-desorption isotherm is a plot of relative pressure vs. volume adsorbed obtained by measuring the amount of $N_2$ gas that adsorbs onto the surface of a sorbate such as 5% Cu—$Ag_3PO_4$, 10% Cu—$Ag_3PO_4$, 15% Cu—$Ag_3PO_4$, and 20% Cu—$Ag_3PO_4$ nanoparticles, and the subsequent amount that desorbs at a constant temperature. The graphs confirm the existence of the mesoporous nanoparticles. The surface area of Cu—$Ag_3PO_4$ nanoparticles was studied by Brunauer-Emmett-Teller (BET) analyzer. The results of the present study are presented in Table 1. From the results as presented in Table 1, it can be observed that the pore volume and surface area of the Cu—$Ag_3PO_4$ nanoparticles increases as the percentage of copper in the nanoparticles increases. Whereas the pore size has an inversely proportional relationship to the percentage of copper in the nanoparticles. The 10% Cu—$Ag_3PO_4$ nanoparticles deviate from this trend by having the largest pore size and smallest pore volume, thereby wide and shallow pores.

TABLE 1 shows surface area, pore size and pore volume for the nanoparticles.

| Samples | Surface area ($m^2/g$) | Pore size (nm) | Pore volume ($cm^3/g$) |
| --- | --- | --- | --- |
| 5% Cu—$Ag_3PO_4$ | 2.959 | 24.42 | 0.016 |
| 10% Cu—$Ag_3PO_4$ | 4.282 | 29.635 | 0.014 |
| 15% Cu—$Ag_3PO_4$ | 6.11 | 19.554 | 0.024 |
| 20% Cu—$Ag_3PO_4$ | 7.0767 | 17.992 | 0.028 |

Figure 7:
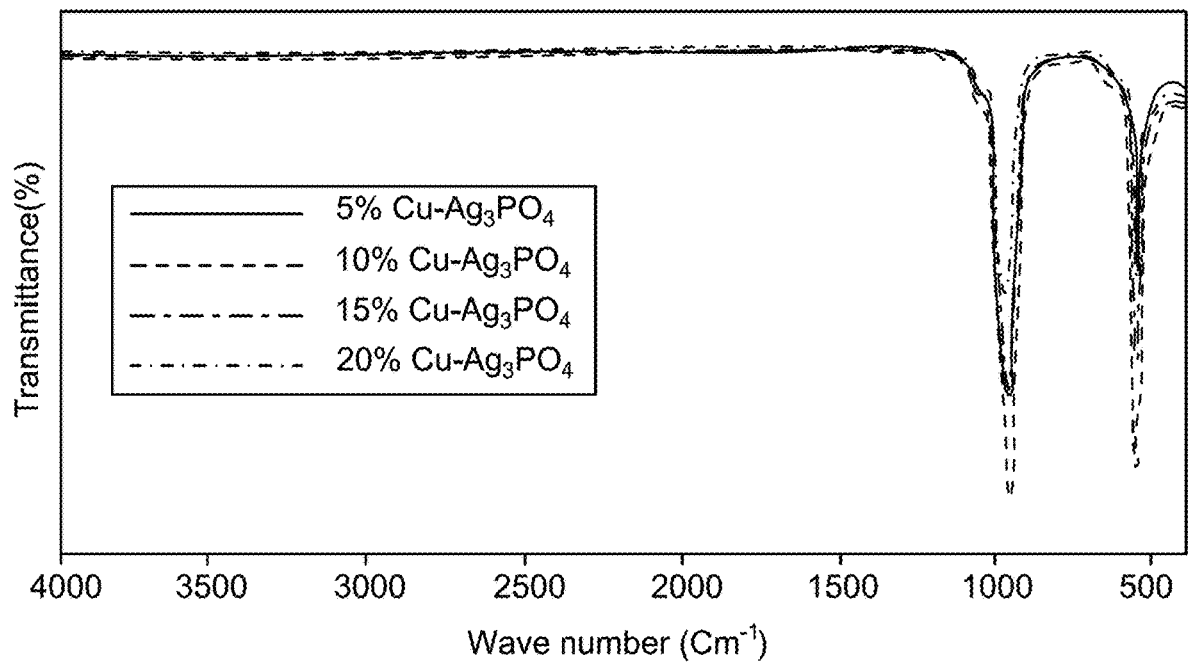
FIG. 7 is a combined Fourier Transform Infrared Spectrum (FTIS) of Cu—$Ag_3PO_4$ nanoparticles with varying weight percentages, according to certain embodiments.

Referring to FIG. 7, a combined Fourier Transform Infrared (FT-IR) spectrum of 5% Cu—$Ag_3PO_4$, 10% Cu—$Ag_3PO_4$, 15% Cu—$Ag_3PO_4$, and 20% Cu—$Ag_3PO_4$ nanoparticles is illustrated. FT-IR spectra are recorded on a Perkin Elmer spectrometer. FT-IR identifies chemical bonds in a molecule by producing an infrared absorption spectrum. The peaks at approximately 900 $cm^{-1}$ and 600 $cm^{-1}$ correspond to P—O bonds in the phosphate groups.

Figure 8:
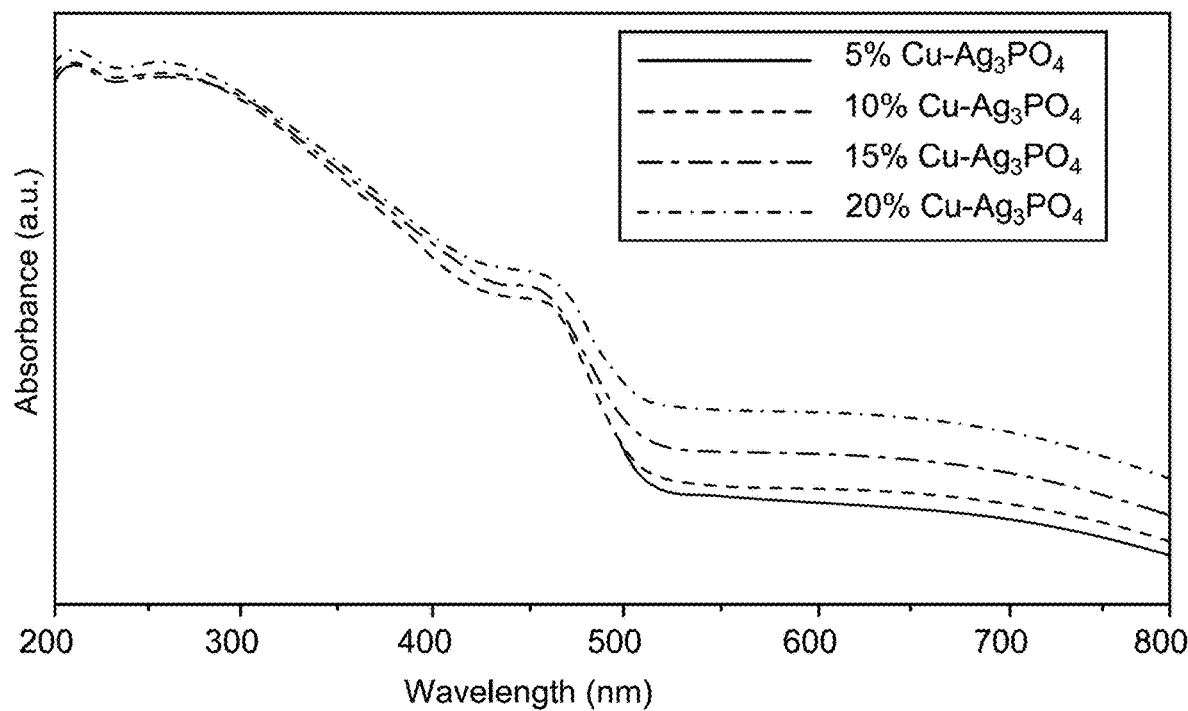
FIG. 8 is a combined Ultraviolet-visible (UV-Vis) spectrum of the Cu—$Ag_3PO_4$ nanoparticles with varying weight percentages, according to certain embodiments.

Referring to FIG. 8, a combined Ultraviolet-visible (UV-vis) spectrum of 5% Cu—$Ag_3PO_4$, 10% Cu—$Ag_3PO_4$, 15% Cu—$Ag_3PO_4$, and 20% Cu—$Ag_3PO_4$ nanoparticles is illustrated. UV-visible spectrophotometer (JASCO V-750) is used to measure diffuse reflectance of Cu—$Ag_3PO_4$ nanoparticles. The spectra show a broad absorption of visible light by the nanoparticles.

Figure 9:
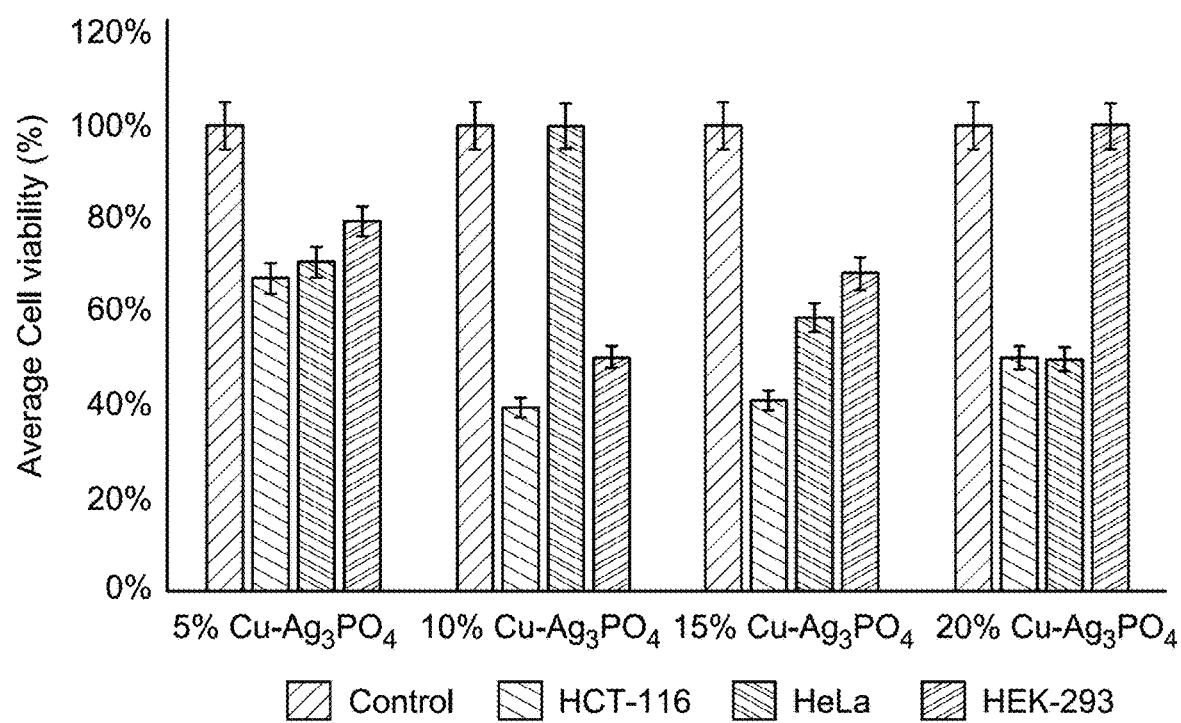
FIG. 9 is a statistical representation of the cell viability assay of control cells and after treatment of HCT-116, HeLa, and HEK-293 cells with Cu—$Ag_3PO_4$ nanoparticles, according to certain embodiments.
Figure 10A:
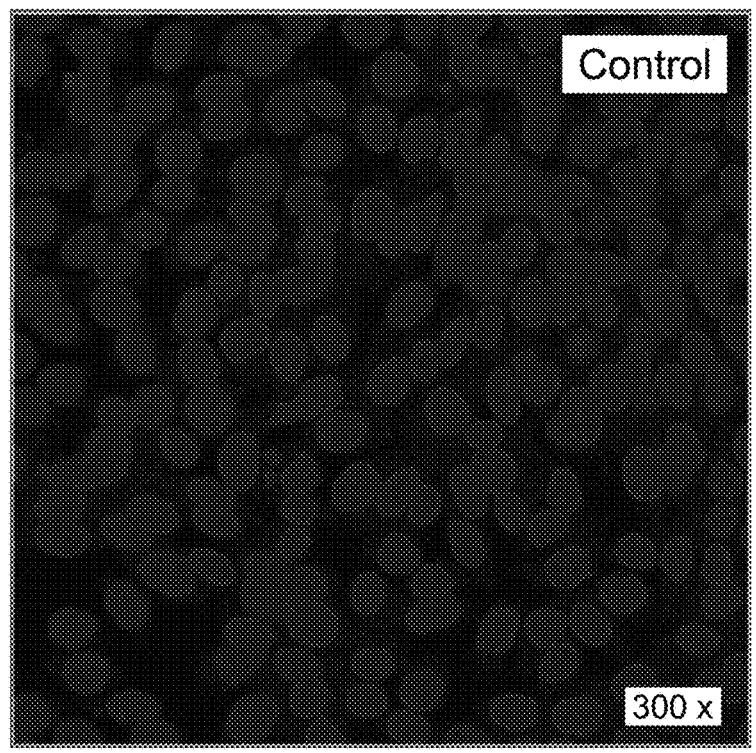
FIGS. 10A-10E are morphological images of colorectal cancer cells (HCT-116) stained with 4',6-diamidino-2-phenylindole (DAPI), 48 hours after treatment with 25 μg/mL of Cu—$Ag_3PO_4$ nanoparticles, Control (10A), 5% Cu—$Ag_3PO_4$ (10B), 10% Cu—$Ag_3PO_4$ (10C), 15% Cu—$Ag_3PO_4$ (10D), 20% Cu—$Ag_3PO_4$ nanoparticles (10E), according to certain embodiments. Arrows show the nuclear condensation, fragmentation, and cell membrane disruption.
Figure 10B:
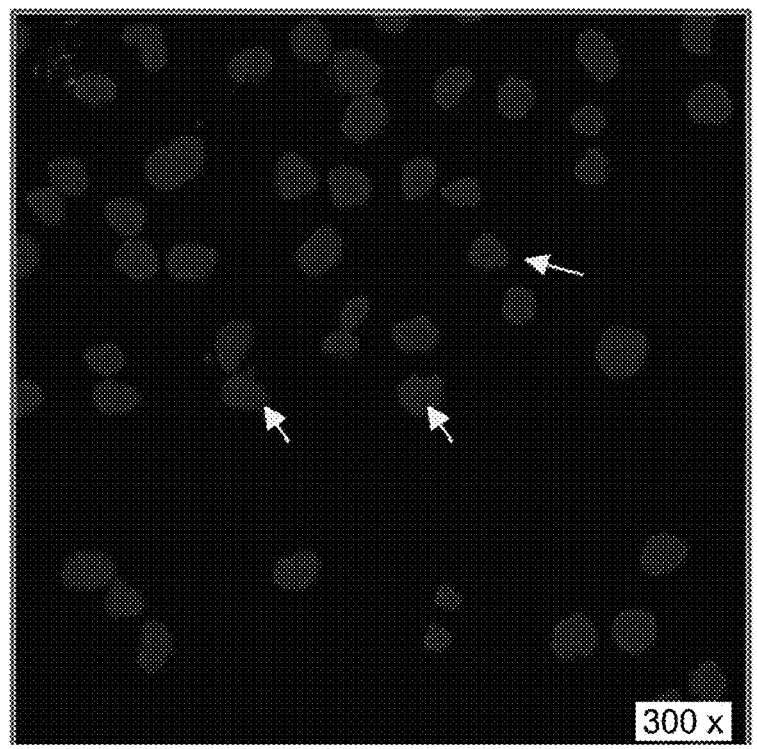
Figure 10C:
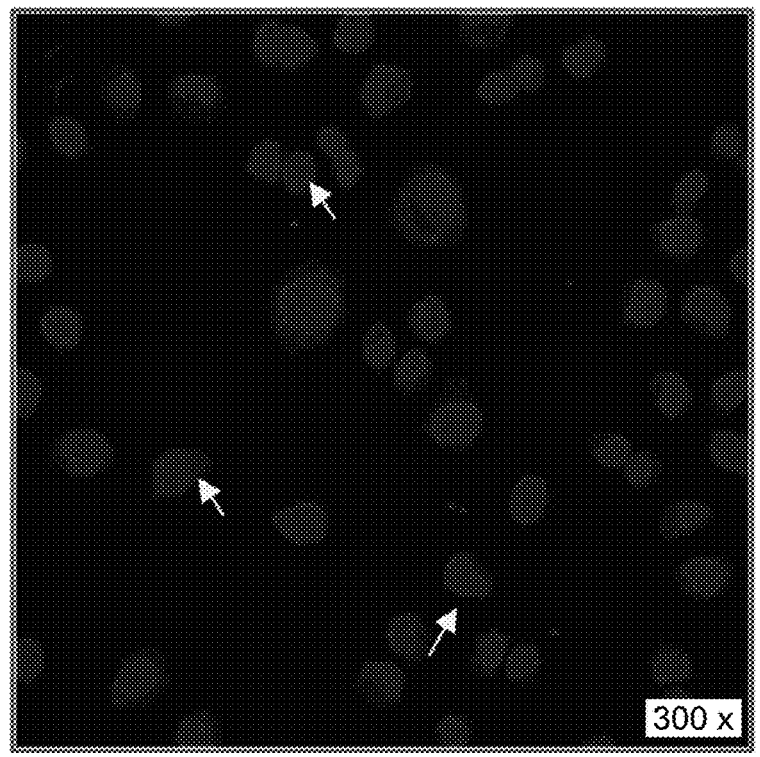
Figure 10D:
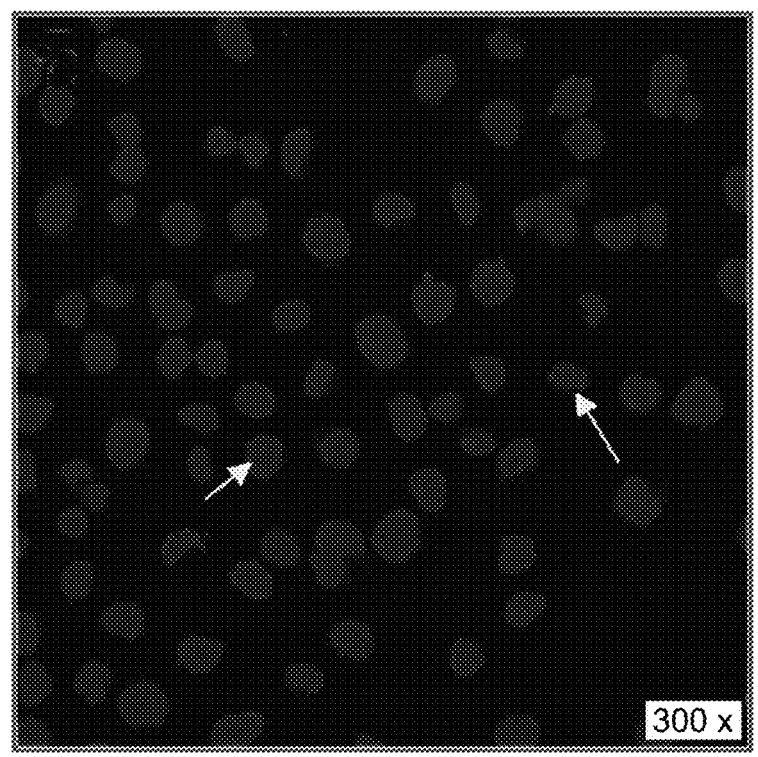
Figure 10E:
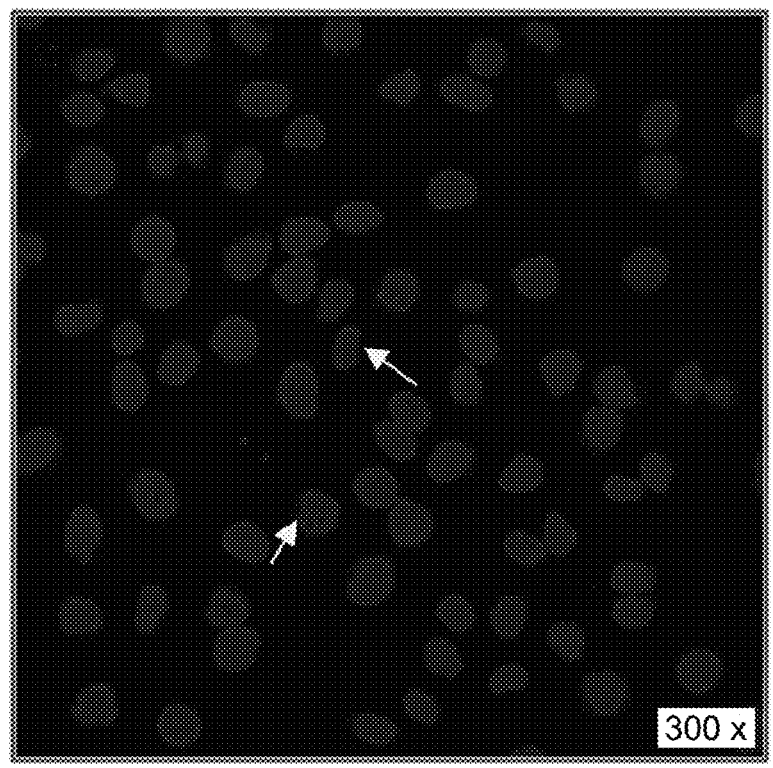

The impact of 5% Cu—$Ag_3PO_4$, 10% Cu—$Ag_3PO_4$, 15% Cu—$Ag_3PO_4$, and 20% Cu—$Ag_3PO_4$ on both colon cancer (HCT-116) and cervical cancer (HeLa) cells was examined by performing cell viability assay and half-maximal inhibitory concentration ($IC_{50}$) studies. A statistical representation of the cell viability assay of control cells and after treatment of HCT-116, HeLa, and HEK-293 cells with Cu—$Ag_3PO_4$ nanoparticles is illustrated in FIG. 9. Cell viability is a measure of the proportion of live, healthy cells within a population. Cell viability assays are used to determine the overall health of cells, establish culture or experimental conditions, and to measure cell survival following treatment with the nanoparticles. For the present purpose, HeLa, HCT-116 and HEK-293 cells (normal cells) stained with DAPI were treated with 5% Cu—$Ag_3PO_4$, 10% Cu—$Ag_3PO_4$, 15% Cu—$Ag_3PO_4$, and 20% Cu—$Ag_3PO_4$ nanoparticles followed by 48-hour treatment. The control cells were not treated with the nanoparticles. As can be observed from the FIG. 9 a significant decrease in colorectal cancer cells viability after treatment with 5% Cu—$Ag_3PO_4$, 10% Cu—$Ag_3PO_4$, 15% Cu—$Ag_3PO_4$, and 20% Cu—$Ag_3PO_4$. The presence of the nanoparticles leads to a decrease of cell viability when compared to a control deprived of any nanoparticles.

The $IC_{50}$ values with 5% Cu—$Ag_3PO_4$, 10% Cu—$Ag_3PO_4$, 15% Cu—$Ag_3PO_4$, and 20% Cu—$Ag_3PO_4$ on HCT-116, HeLa cells and HEK-293, were studied and the results of the present study are presented in Table 2. $IC_{50}$ is a quantitative measure that indicates how much of a particular inhibitory substance, in this study Cu—$Ag_3PO_4$ nanoparticles, is needed to inhibit cell viability by 50%.

TABLE 2

IC$_{50}$ value for Cu—Ag$_3$PO$_4$ nanoparticles (5, 10, 15 and 20%) on HCT-116, HeLa cells and HEK-293

| Samples | HCT-116 (IC$_{50}$ (μg/mL)) | HeLa (IC$_{50}$ (μg/mL)) | HEK-293 (IC$_{50}$ (μg/mL)) |
|---|---|---|---|
| 5% Cu—Ag$_3$PO$_4$ | 67.00 ± 1.0 μg/mL | 70.83 ± 2.2 μg/mL | 79.51 ± 8.2 μg/mL |
| 10% Cu—Ag$_3$PO$_4$ | 40.00 ± 4.2 μg/mL | 100.00 ± 4.2 μg/mL | 50.00 ± 4.2 μg/mL |
| 15% Cu—Ag$_3$PO$_4$ | 41.00 ± 5.2 μg/mL | 58.87 ± 4.2 μg/mL | 68.30 ± 4.2 μg/mL |
| 20% Cu—Ag$_3$PO$_4$ | 50.00 ± 4.2 μg/mL | 50.00 ± 4.2 μg/mL | 100.00 ± 4.2 μg/mL |

The IC$_{50}$ value for 5% Cu—Ag$_3$PO$_4$, 10% Cu—Ag$_3$PO$_4$, 15% Cu—Ag$_3$PO$_4$, and 20% Cu—Ag$_3$PO$_4$ on HCT-116, HeLa cells and HEK-293 IC$_{50}$ was calculated, and it was observed to be in the range 40-100 μg/mL. From Table 2, it can be observed that in most cases, a lower concentration of Cu—Ag$_3$PO$_4$ nanoparticles is required to inhibit cancer cell viability as the amount of copper in the nanoparticle increases. Also, overall the IC$_{50}$ values are higher for normal HEK-293 than the cancer cells, therefore the nanoparticles have a higher affinity for cancer cells, especially the 20% Cu—Ag$_3$PO$_4$ which caused damage to the normal cells at a high concentration. The 10% Cu—Ag$_3$PO$_4$ nanoparticles have the lowest IC$_{50}$ value for the HCT-116 cells, indicating that their wide and shallow pores may have a stronger interaction with the HCT-116 cells.

FIGS. 10A-10E refer to morphological images of HCT-116 cells stained with DAPI post 48-hour treatment. FIGS. 10A-10E depict control cells; HCT-116 cells treated with 5% Cu—Ag$_3$PO$_4$; HCT-116 cells treated with 10% Cu—Ag$_3$PO$_4$; HCT-116 cells treated with 15% Cu—Ag$_3$PO$_4$; and HCT-116 cells treated with 20% Cu—Ag$_3$PO$_4$, respectively, with a dose of 25 μg/mL. The images show a decrease in the number of cells, nuclear condensation, fragmentation, and cell membrane disruption after exposure to Cu—Ag$_3$PO$_4$ nanoparticles. This clearly demonstrates that the Cu—Ag$_3$PO$_4$ nanoparticles are effective in decreasing cell viability even at μg/mL dosages.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method of decreasing cancer cell viability colorectal cancer cells in a cell culture, comprising:
   contacting, in vitro, a Cu—Ag$_3$PO$_4$ composition to the colorectal cancer cells and incubating in a CO$_2$ incubator,
   wherein the Cu—Ag$_3$PO$_4$ composition comprises substantially spherical Cu—Ag$_3$PO$_4$ nanoparticles having a mean particle size of 100-1,000 nm,
   wherein an amount of the Cu—Ag$_3$PO$_4$ nanoparticles is 5.0 to 95 g per mL of the cell culture,
   wherein the Cu—Ag$_3$PO$_4$ nanoparticles have an IC$_{50}$ of 36-46 μg per mL of the cell culture,
   wherein the colorectal cancer cells are HCT-116 cells,
   wherein copper is present in the Cu—Ag$_3$PO$_4$ nanoparticles in an amount of 10-15 weight percent (wt. %) based on the total weight of the Cu—Ag$_3$PO$_4$ nanoparticles.

2. The method of claim 1, wherein the contacting is for 48 hours.

3. The method of claim 2, wherein the colorectal cancer cells are incubated in the CO$_2$ incubator for 4 hours.

4. The method of claim 1, wherein the Cu—Ag$_3$PO$_4$ nanoparticles have a BET mean surface area of 4.2-6.1 m$^2$/g.

5. The method of claim 4, wherein the Cu—Ag$_3$PO$_4$ nanoparticles have a BET mean pore size of 19.5-29.6 nm.

6. The method of claim 1, wherein during the contacting the Cu—Ag$_3$PO$_4$ nanoparticles are aggregated.

7. The method of claim 1, wherein the Cu—Ag$_3$PO$_4$ nanoparticles have a mean particle size of 200-300 nm.

* * * * *